(12) United States Patent
Dambrin et al.

(10) Patent No.: US 7,619,116 B2
(45) Date of Patent: Nov. 17, 2009

(54) INTERMEDIATES FOR THE SYNTHESIS OF (R)-TAMSULOSIN AND OF ITS PHARMACEUTICALLY ACCEPTABLE SALTS AND PROCESS FOR THEIR PREPARATION

(75) Inventors: Valéry Dambrin, Montreuil Juigne (FR); Jean-Yves Lenoir, Perdreauville (FR); Jean-Marie Schneider, Magnanville (FR); Gérard Guillamot, Viroflay (FR); Michel Follet, Avignon (FR); Abram Becker, Paris (FR)

(73) Assignee: Products Chimiques Auxiliaires Et de Synthese, Longjumeau (FR)

( * ) Notice: Subject to any disclaimer, the term of this patent is extended or adjusted under 35 U.S.C. 154(b) by 91 days.

(21) Appl. No.: 10/583,472

(22) PCT Filed: Dec. 15, 2004

(86) PCT No.: PCT/IB2004/004358

§ 371 (c)(1),
(2), (4) Date: Jun. 19, 2006

(87) PCT Pub. No.: WO2005/058810

PCT Pub. Date: Jun. 30, 2005

(65) Prior Publication Data

US 2007/0106079 A1    May 10, 2007

(30) Foreign Application Priority Data

Dec. 17, 2003   (FR) .................................. 03 14793

(51) Int. Cl.
*C07C 211/08* (2006.01)
(52) U.S. Cl. ....................................................... 564/347
(58) Field of Classification Search .................. 564/347
See application file for complete search history.

(56) References Cited

U.S. PATENT DOCUMENTS 4,971,990 A * 11/1990 Itoh et al. .................... 514/408
2003/0207934 A1* 11/2003 Or et al. ...................... 514/423

FOREIGN PATENT DOCUMENTS

| JP | 2000 229901 A | 8/2000 |
| WO | WO-03/035608 A | 5/2003 |
| WO | WO-03/093227 A1 | 11/2003 |

OTHER PUBLICATIONS

Sakurai et al., Chem. Pharm. Bull., vol. 40, No. 6, pp. 1443-1451 (1992) (XP-002291914).
B.G. Donner, Conversion of chiral amino acids to enantiomerically pure alpha-methylamines, Tetrahedon Letters, Feb. 20, 1995, pp. 1223-1226, vol. 36-No. 8.

* cited by examiner

*Primary Examiner*—Rebecca L Anderson
*Assistant Examiner*—Shawquia Young
(74) *Attorney, Agent, or Firm*—Birch, Stewart, Kolasch & Birch, LLP

(57) ABSTRACT

A subject matter of the present invention is novel intermediates for the synthesis of (R)-tamsulosin and of its pharmaceutically acceptable salts, and also the associated preparation process.

12 Claims, No Drawings

INTERMEDIATES FOR THE SYNTHESIS OF (R)-TAMSULOSIN AND OF ITS PHARMACEUTICALLY ACCEPTABLE SALTS AND PROCESS FOR THEIR PREPARATION

A subject matter of the present invention is novel intermediates for the synthesis of (R)-tamsulosin and of its pharmaceutically acceptable salts, and also the associated preparation process.

(R)-Tamsulosin is also known under the chemical name of (R)-(−)-5-[2-[2-(2-ethoxyphenoxy)ethylamino]propyl]-2-methoxybenzenesulfonamide. Tamsulosin was discovered by Yamanouchi and has thus been disclosed in patent EP 0 034 432. It is a powerful and selective antagonist of $\alpha_1$ adrenergic receptors. Tamsulosin relaxes smooth muscles in cases of benign prostatic hyperplasia, produces an increase in urinary flow rate and improves obstructive symptoms.

Tamsulosin is thus regarded as one of the best antagonists and is therefore very widely used in numerous countries. It is in reality the (R) enantiomer which proves to be the most advantageous enantiomer in terms of ratio of therapeutic benefit with respect to side effects; for this reason, efforts are concentrated on the synthesis of this enantiomer.

Various processes for the synthesis of (R)-tamsulosin have been described in the literature.

The synthesis of (R)-tamsulosin is relatively complex and is conventionally based on the preparation of a chiral amine, (R)-5-(2-aminopropyl)-2-methoxybenzenesulfonamide, obtained in 14 stages from anisaldehyde and nitroethane. This amine is rendered optically active by resolution using a salt of an optically active acid and is subsequently condensed with a 2-(2-ethoxyphenoxy)ethanol derivative, such as 1-bromo-2-(2-ethoxyphenoxy)ethane or 2-(2-ethoxyphenoxy)acetaldehyde, or alternatively 2-(2-ethoxyphenoxy)acetyl chloride. Of course, in the case of the aldehyde or of the acid chloride, the condensation is followed by a reduction stage.

This synthesis suffers from two major disadvantages:

1. The asymmetric intermediate (R)-1-(4-methoxyphenyl)-2-aminopropane is obtained from a racemic compound and thus requires a resolution stage. The resolution is obtained either by the formation of a salt of an asymmetric acid (diastereoisomers), followed by several selective crystallizations, or by the formation of an imine (R)-1-(4-methoxyphenyl)-N-(1-phenylethyl)-2-propanimine, followed by a reduction, several crystallizations and a hydrogenolysis, in order to obtain a satisfactory optical purity, and 2. The final condensation, between the key intermediate (R)-5-(2-aminopropyl)-2-methoxybenzenesulfonamide and 1-bromo-2-(2-ethoxyphenoxy)ethane, takes place with a mediocre yield. When it is carried out with 2-(2-ethoxyphenoxy)acetaldehyde, the yield is fairly good but then requires an additional stage of reduction by catalytic hydrogenation or by borohydride. Condensation with the acid chloride, namely 2-(2-ethoxyphenoxy)acetyl chloride, is satisfactory but requires a reduction with a two-fold amount of sodium borohydride ($NaBH_4$) or lithium aluminum hydride ($LiAlH_4$).

More recently, patent application WO 03/0356608 discloses an improvement to this synthetic route where the coupling is carried out with 1-bromo-2-(2-ethoxyphenoxy)ethane in a specific molar ratio.

The Applicant Company has thus looked for a novel process which overcomes the abovementioned disadvantages, making possible simpler, more economic and more reliable implementation.

(R)-Tamsulosin has the following chemical formula:

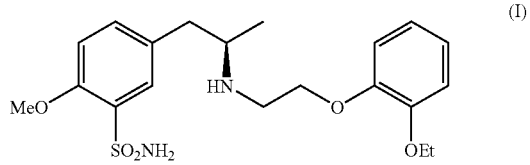

(I)

A first subject matter of the present invention is thus a novel process for the preparation of a novel intermediate for the synthesis of (R)-tamsulosin and of its pharmaceutically acceptable salts, and also all its alternative forms.

Another subject matter of the invention is novel compounds used in particular as intermediates in the synthesis of (R)-tamsulosin and of its pharmaceutically acceptable salts. Mention may be made, among pharmaceutically acceptable salts of (R)-tamsulosin, of the hydrochloride, which is preferred, but also those commonly used, such as described in Handbook of Pharmaceutical Salts, P. H. Stahl and C. G. Wermuth Eds. (Wiley VCH, Weinheim, VHCA, Zürich), 2002.

More particularly, mention may be made, as salts acceptable for the therapeutic use, of conventional nontoxic salts, such as those formed from organic or inorganic acids. Mention may be made, for example, of the salts derived from inorganic acids, such as hydrochloric acid, hydrobromic acid, phosphoric acid or sulfuric acid, and those derived from organic acids, such as acetic acid, trifluoroacetic acid, propionic acid, succinic acid, fumaric acid, malic acid, tartaric acid, citric acid, ascorbic acid, maleic acid, glutamic acid, benzoic acid, salicylic acid, toluenesulfonic acid, methanesulfonic acid, stearic acid or lactic acid.

The invention also relates to a process for the synthesis of (R)-tamsulosin and of its pharmaceutically acceptable salts.

The process according to the first subject matter of the invention consists in reacting a compound of formula (IV)

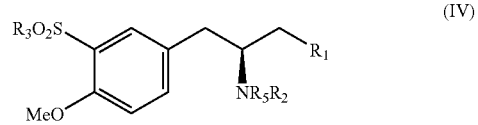

(IV)

in which $R_1$ represents a halogen or an —$SR_4$ or —$OR_4$ group, $R_5$ and $R_2$ represent, simultaneously or independently of one another, a hydrogen atom or a ($C_1$-$C_7$)alkyl, aryl, ($C_1$-$C_7$) alkylaryl, ($C_1$-$C_7$)alkyloyl, aryloyl, ($C_1$-$C_7$)alkyl-oxycarbonyl or aryloxycarbonyl group, —$NR_5R_2$ can also represent an —$NHR_2$ group where $R_2$ is a protective group Pg as defined below, or $R_1$ and $R_2$ together form an oxazolidin-2-one, thiazolidin-2-one or thiazolidine-2-thione group, $R_3$ represents a halogen atom or an —$NR_5R_2$ group as defined above, and $R_4$ represents a hydrogen atom, a ($C_1$-$C_7$)alkyl, aryl, ($C_1$-$C_7$) acyloyl or aryloyl group or, regarding the —$SR_4$ functional group, an isothiocyanate, aryl sulfone or thioamidine group or, regarding the —$OR_4$ functional group, a ($C_1$-$C_7$) alkylisourea, tri($C_1$-$C_7$)alkylsilyloxy, tosyl, mesyl, nosyl, trifluoromethanesulfonyl or trifluoroacetyl group, with a compound of formula (III),

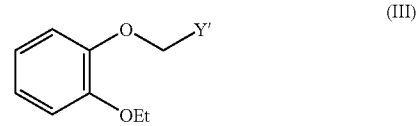

(III)

in which
- Y' represents a —CO₂H, —COCl, —CHO, —CH₂Cl, —CH₂Br or —CH₂I group when the coupling takes place with a compound of formula (IV) for which R₁ is a —SR₄ or —OR₄ group,
- or Y' represents a —CHO group when the coupling takes place with a compound of formula (IV) for which R₁ is a —SH or —SR₄ group,
- or Y' represents a —COCl, —CH₂Cl, —CH₂Br or —CH₂I group when the coupling takes place with a compound of formula (IV) for which the R₁ and R₂ groups together form an oxazolidin-2-one, a thiazolidin-2-one or a thiazolidine-2-thione,
- or, finally, Y' represents a —CS₂Na group when the coupling takes place with a compound of formula (IV) for which R₁ is a halogen atom or a leaving group, such as tosyl, mesyl, trifluoroacetyl, nosyl, or trifluoromethanesulfonyl;

in order to obtain the compound of formula (II),

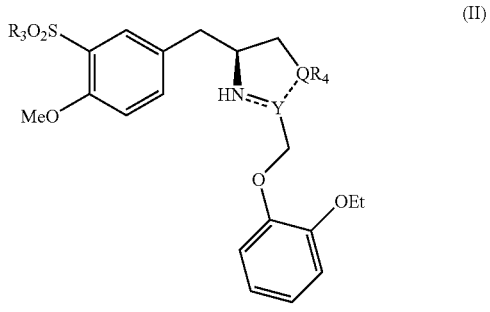

in which
Q represents an oxygen or sulfur atom,
R₃ and R₄ are as defined above, and
when - - - - - means that there does not exist a bond so as to form a ring, Y represents

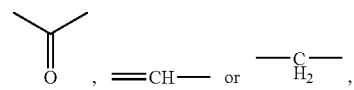

when - - - - - means that there exists a bond so as to form a ring,
Y represents

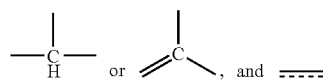

means that there exists a single bond or a double bond, according to the following scheme 1:

Scheme 1

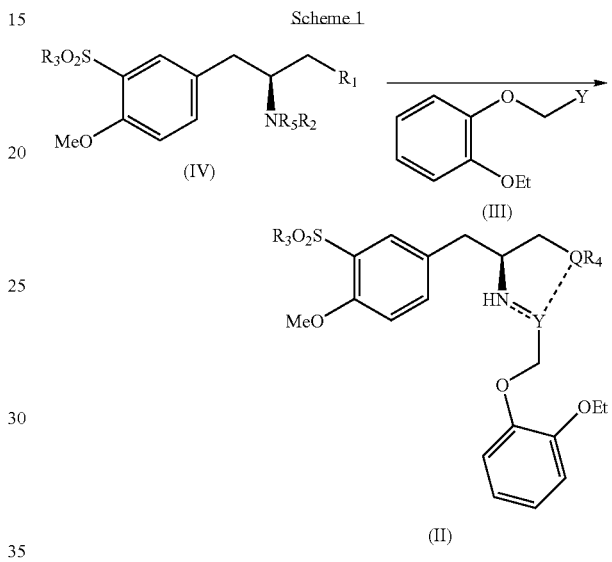

This coupling process, and all its alternative forms, form part of the present invention.

The coupling process according to the invention is illustrated by scheme 2, which describes the various access routes to the compound of formula (II) and the associated main stages.

Scheme 2

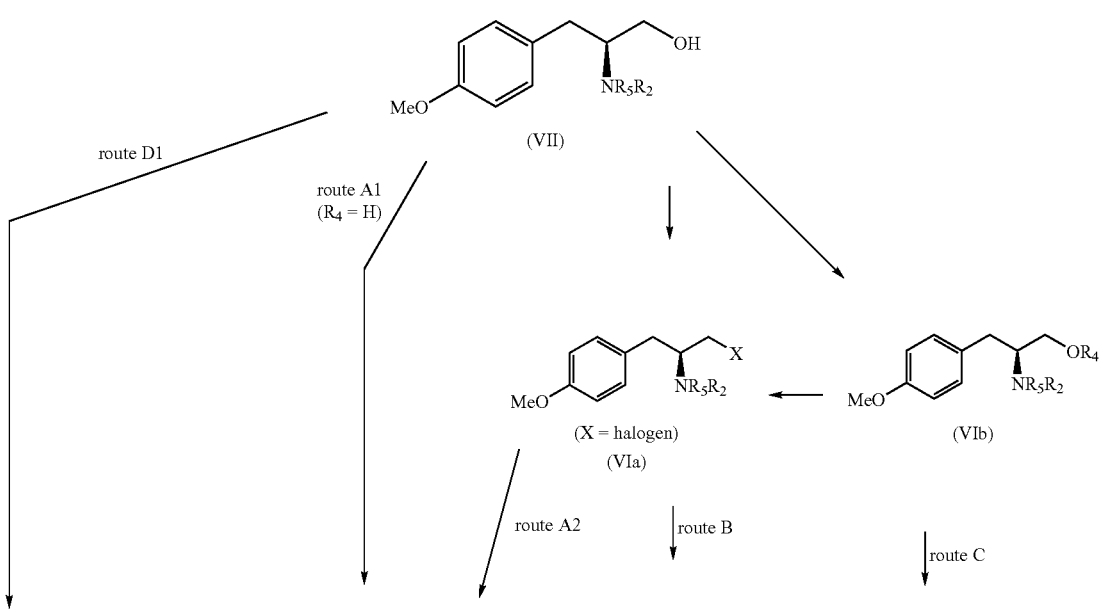

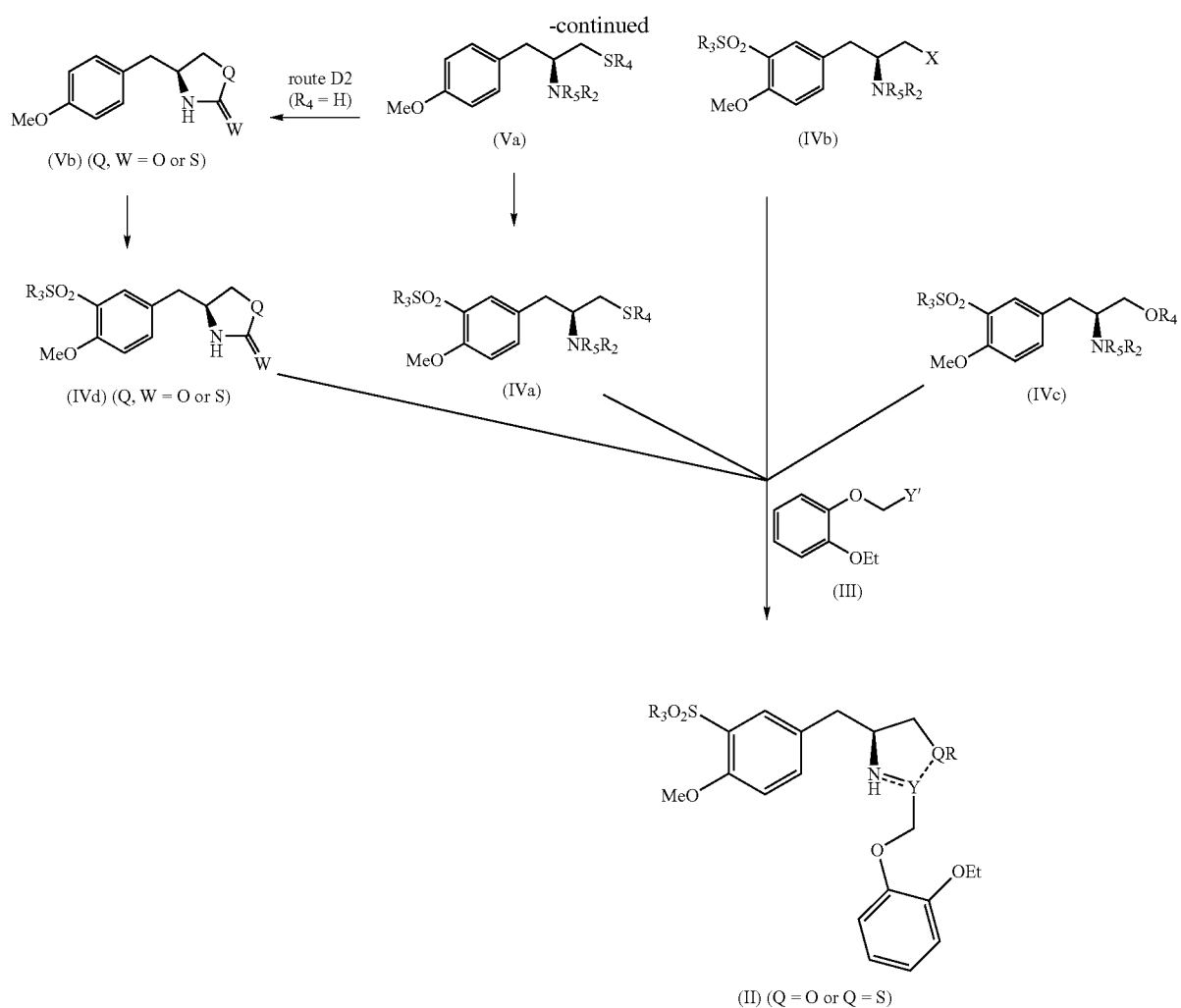

Starting from the (S)-N-acetyl-O-methyltyrosinol derivative (VII), it is thus possible to obtain, in several stages, the key intermediate of formula (IV), available as four compounds (IVa), (IVb), (IVc) or (IVd) depending on the possible meanings of the $R_1$ substituent described above, which makes it possible to carry out the coupling stage in order to obtain the intermediate compound (II), which results in (R)-tamsulosin after a final treatment, according to the explanations given below in the description.

In the context of the present invention:

- the term "an alkyl group" is understood to mean an alicyclic or nonalicyclic linear or branched saturated aliphatic group. Mention may in particular be made of the methyl, ethyl, propyl, isopropyl, butyl, isobutyl, tert-butyl or cyclohexyl groups, and the like,
- the term "a halogen" is understood to mean a fluorine, chlorine, bromine or iodine atom,
- the term "a protective group Pg" is understood to mean a group which makes it possible, first, to protect a reactive functional group, such as a hydroxyl or an amine, during the synthesis, and, secondly, to regenerate the reactive functional group intact at the end of the synthesis. Examples of protective groups and the methods of protection and deprotection are given in Protective Groups in Organic Synthesis, Green et al., $3^{rd}$ Ed. (John Wiley & Sons Inc., New York). Preference is given, in the context of the present invention, as regards the amine functional group, to the acetyl, benzyl, tert-butoxycarbonyl, benzyloxycarbonyl, trifluoroacetyl, benzoyl, dinitrobenzoyl, neohexanoyl or phthaloyl group, in particular, and to the acetyl, mesyl, tosyl, tri($C_1$-$C_7$)alkylsilyl or ($C_1$-$C_7$)alkylisourea groups, and the like, as regards the alcohol functional group,
- the term "an aryl group" is understood to mean a system having 1 or 2 aromatic rings, such as the phenyl, naphthyl, tetrahydronaphthyl or indanyl group. These rings can be substituted with 1 to 3 groups chosen from a ($C_1$-$C_3$)alkyl group, a ($C_1$-$C_3$)alkoxy group, an amino group, a halogen or a nitro, hydroxyl, ($C_1$-$C_2$)alkylamino, ($C_1$-$C_3$)alkyloyl, ($C_1$-$C_3$)alkyloxycarbonyl, ($C_1$-$C_3$)alkylamido or trihalomethyl group.

The operating conditions of the coupling stage, and in particular the various access routes A1, A2, B, C, D1 and D2, are described below in more detail.

It is obvious that the operating conditions for the coupling of the compounds (IV) and (III) to give the compound (II) depend on the meanings of the substituents.

When $R_1$, substituent of the compound of formula (IV), represents an —$SR_4$ or —$OR_4$ group, $R_4$ being as defined above, namely the compound of formula (IV) is of (IVa) or (IVc) type, the coupling can be carried out with a compound of formula (III) where Y' represents a —$CO_2H$, —COCl, —CHO, —$CH_2Cl$, —$CH_2Br$ or —$CH_2I$ group, in the presence or absence of a reducing agent, such as sodium borohydride or its derivatives or lithium aluminum hydride or its derivatives, or of a metal catalyst (nickel, palladium or platinum) under a hydrogen atomsphere or of a coupling agent, such as, for example, dicyclohexylcarbodiimide, N-hydroxysuccinimide or hydroxybenzotriazole or one of its derivatives, with or without catalysts, such as 4-dimethylaminopyridine, or of an organic or inorganic base, such as, for example, triethylamine or sodium hydrogencarbonate, in a solvent, such as, for example, methanol, ethanol, tetrahydrofuran, diethyl ether or N,N-dimethyl-formamide. The reaction can last between 1 hour and 24 hours. Generally, the molar ratio of the compound of formula (IV) to the compound of formula (III) is between 0.8 and 1.1, preferably between 0.9 and 1.0. The reaction temperature is generally between 0° C. and the reflux temperature of the solvent used.

When $R_1$, substituent of the compound of formula (IV), represents an —SH or —$SR_4$ group, $R_4$ being as defined above, namely the compound of formula (IV) is of (IVa) type, the coupling can be carried out with a compound of formula (III) where Y' represents a —CHO group, in the presence of a reducing agent, such as sodium borohydride, sodium cyanoborohydride or lithium aluminum hydride, or under a hydrogen atmosphere in the presence of a metal catalyst, such as palladium, platinum or nickel, in a solvent, such as, for example, methanol, ethanol, tetrahydrofuran or diethyl ether. The reaction can last between 1 hour and 24 hours. Generally, the molar ratio of the compound of formula (IV) to the compound of formula (III) is then between 0.8 and 1.1, preferably between 0.9 and 1.0. The reaction temperature is generally between 0° C. and the reflux temperature of the solvent used.

When $R_1$, substituent of the compound of formula (IV), represents a halogen atom or a leaving group, such as, for example, mesyl, tosyl, nosyl, trifluoroacetyl or trifluoromethanesulfonyl, namely the compound of formula (IV) is of (IVb) or (IVc) type, the coupling can be carried out with a compound of formula (III) where Y' represents a —$CS_2Na$ group, in a solvent, such as methanol, ethanol, water or any mixture of these constituents. The reaction can last between 1 hour and 24 hours at a temperature of between 20° C. and 100° C. and a strong acid, such as hydrochloric acid, or triphenylphosphine can be added to the reaction medium so as to shift the reaction equilibrium. Generally, the molar ratio of the compound of formula (IV) to the compound of formula (III) is between 0.8 and 1.1, preferably between 0.9 and 1.0.

When $R_1$ and $R_2$, substituents of the compound of formula (IV), together form an oxazolidin-2-one, a thiazolidin-2-one or a thiazolidine-2-thione, namely the compound of formula (IV) is of (IVd) type, the coupling can be carried out with a compound of formula (III) where Y' represents a —COCl, —$CH_2Cl$, —$CH_2Br$ or —$CH_2I$ group, in the presence of an organic or inorganic base, such as, for example, sodium hydride, potassium tert-butoxide, potassium carbonate or cesium carbonate, in a solvent, such as tetrahydrofuran, acetone, N,N-dimethyl-formamide, N,N-dimethylacetamide, N-methylpyrrolidinone or dimethyl sulfoxide. The reaction can last between 1 hour and 24 hours at a temperature of between 20° C. and 140° C. Generally, the molar ratio of the compound of formula (IV) to the compound of formula (III) is between 0.8 and 1.1, preferably between 0.9 and 1.0. After coupling, the reaction is brought to completion, in order to result in the compound (II), either by treatment with a strong acid, such as, for example, aqueous hydrochloric acid, at 100° C., or in the presence of a strong inorganic base, such as potassium hydroxide, in a solvent, such as ethylene glycol, propylene glycol or diglyme, at a temperature between 50° C. and 150° C.

As regards the access routes to the compound of formula (IV) which are illustrated in scheme 2 described above, the operating conditions of each of them are described as follows:

The stage of producing the compound of formula (VIa) from the compound of formula (VII), of use for the synthetic routes A2 and B, can be carried out according to the usual rules of chemistry, such as the action of an inorganic or organic halide, for example thionyl chloride, thionyl bromide, phosphorus trichloride, phosphorus tribromide, phosphorus pentachloride, phosphorus oxychloride, oxalyl chloride, phosphorus iodide, halogen/triphenylphosphine complexes, iodotrimethylsilane or chlorotrimethylsilane, in the presence of alkali metal iodide or phosphoric acid in combination with potassium iodide.

When $R_4$ is the hydrogen atom, it is possible, according to synthetic route A1, to directly obtain a compound of formula (Va) without passing through the compound of formula (VIa), namely the halogenated derivative, by reacting the compound of formula (VII) with a dithiophosphonic acid, such as diethoxydithiophosphonic acid, according to the Mitsunobu method, or with phosphorus pentasulfide or alternatively with triarylphosphine sulfides or their derivatives, according to the Lawesson method.

When $R_1$ and $R_2$ together form an oxazolidin-2-one, a thiazolidin-2-one or a thiazolidine-2-thione, the compound of formula (Vb) can be obtained directly from the compound of formula (VII), according to synthetic route D1, or from the derivative (Va), according to synthetic route D2. It is possible to carry out this conversion, widely described in the literature, when Q is an oxygen, with conventional reactants, such as, for example, phosgene, diethyl carbonate or carbonyldiimidazole, and then optionally to treat the oxazolidinone thus obtained with, for example, potassium thiolacetate, phosphorus pentasulfide or alternatively with triarylphosphine sulfides or their derivatives, according to the Lawesson method, if it is desired to prepare the corresponding sulfur derivatives for which Q is a sulfur.

Chlorosulfonation, which makes it possible to obtain the compounds of formula (IVa) from the compound of formula (Va) or (IVd) from (Vb) or (IVb) from the compound of formula (VIa) or (IVc) from the compound of formula (VIb), can be carried out according to methods known to a person skilled in the art, such as that employing sulfuric acid or oleum, followed by treatment with phosphorus pentachloride, or alternatively chlorosulfonic acid alone. In the case of the derivatives of sulfonamide type, they can advantageously be prepared from the sulfonyl chloride ($R_3$=Cl) using gaseous ammonia or ammonia in aqueous solution, ammonium carbonate or alternatively an amine, such as, for example, benzylamine or benzhydrylamine.

The compound of formula (VIb) can be obtained from the compound of formula (VII) by reacting the latter with various alkylating or acylating agents, such as alkyl halides, chlorotrialkylsilanes, acyl chlorides, anhydrides, alkylsulfonyl chlorides and arylsulfonyl chlorides.

All the methods which make it possible to obtain the derivatives (IV) where $R_5$ and $R_2$ are such that they represent a protective group are subsequently followed by a final deprotection stage conventionally described in the literature.

It is thus possible to obtain the derivatives (IV) where $R_5$=$R_2$=H by acidic or basic treatment or, for example, by methods such as methylhydrazine, as concerns the phthaloyl group.

It is synthetic route A2 which is preferred in the context of the present invention.

In other words, preferably, $R_1$ represents an —$SR_4$ group where $R_4$ is a ($C_1$-$C_7$)alkyl and more preferably still a methyl group.

In order to obtain the compound of formula (VIa) from the compound of formula (VII), use is advantageously made of thionyl chloride at ambient temperature, followed by heating the reaction medium. Use may also be made, during this stage, of phosphorus trichloride, phosphorus pentachloride, phosphorus oxychloride or oxalyl chloride, according to a method known to a person skilled in the art. The compound (VIa) can also be prepared via the intermediate (VIb) where $R_4$ can be an acetyl group or one of its trihaloacetyl derivatives, a perfluoroalkylcarbonyl group, a mesyl group, a tosyl group or one of their derivatives.

According to an advantageous alternative form of the process which is a subject matter of the present invention, the compound of formula (IV) can be obtained from a compound of formula (V)

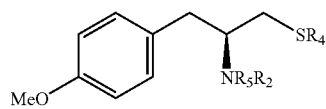

(V)

itself obtained by acylation of a compound of formula (VII)

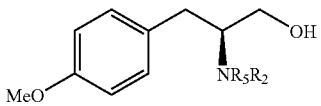

(VII)

resulting in a compound of formula (VIb)

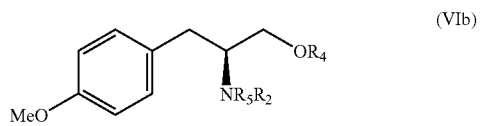

(VIb)

itself subjected to a chlorination reaction, resulting in a compound of formula (VI)

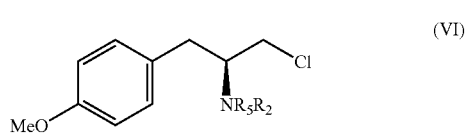

(VI)

itself subjected to a thioalkylation reaction, resulting in the said compound of formula (V), the $R_2$, $R_3$, $R_4$ and $R_5$ radicals having the same meanings as those given above.

The acylating agents used during the operation for the conversion of the compounds of formula (VII) to compounds of formula (VIb) are preferably acyl anhydride, acyl halides, in particular acyl chlorides, or sulfonyl halides, in particular sulfonyl chlorides.

The chlorination operation for the conversion of the compounds of formula (VIb) to compounds of formula (VI) should advantageously be carried out by use of a metal chloride, for example by use of lithium chloride.

The stage for producing the compound of formula (Va) in which the $R_4$ group is other than a hydrogen atom, namely is a ($C_1$-$C_7$)alkyl group and preferably a methyl group, can be carried out either by the action of a basic salt of an alkyl mercaptan, such as sodium methylthiolate, or by the action of a salt of a thiocarboxylic acid, such as potassium thioacetate, or alternatively by salts of a dithiocarboxylic acid or of a dithiocarbonate, such as potassium ethyl dithiocarbonate, on the compound of formula (VIa).

Use is preferably made of chlorosulfonic acid to introduce the —$SO_2Cl$ group onto the benzene ring. Other reactants can also be used, such as sulfuric acid or oleum, followed by treatment with phosphorus pentachloride, or alternatively chlorosulfonic acid.

It is subsequently ammonia which makes it possible to result in the compound of formula (IVa'), followed by addition of strong acid, such as hydrochloric acid, to produce the compound of formula (IVa").

The coupling can subsequently be carried out under the operating conditions described above and the desulfurization according to the operating conditions described below.

This access route is described in more detail by virtue of the following scheme 3, where the compound of formula (III) employed during the coupling stage is that for which Y is a —CHO group, in other words when the compound of formula (III) is an aldehyde, which constitutes a very preferred route for the synthesis of (R)-tamsulosin in the context of the present invention.

Scheme 3

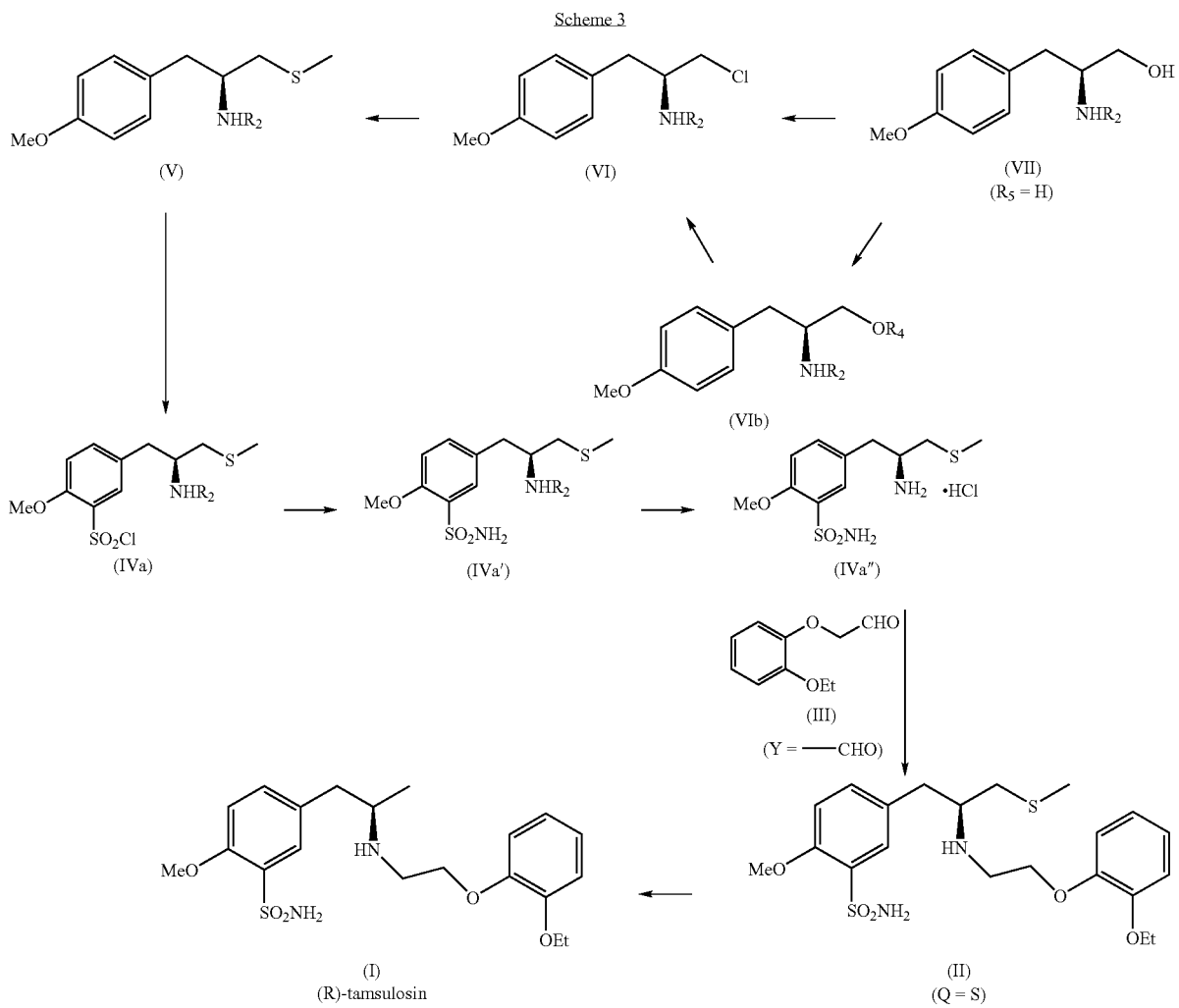

During the final stage following the coupling stage which is a subject matter of the present invention, the compound of formula (II), when Q represents a sulfur atom, is desulfurized, which results directly in (R)-tamsulosin of formula (I). This desulfurization can, for example, take place in the presence of Raney nickel or of its nickel/aluminum alloy, of the zinc/nickel chloride alloy or of nickel boride, optionally in the presence of a catalytic amount of sodium borohydride, at a temperature of between 0° C. and 80° C. When a cyclic compound of formula (II), exhibiting a C—N double bond, is obtained, a reduction stage may be added before the desulfurization stage, although it can be concomitant with the desulfurization when the reducing agents are sufficiently powerful, which is in particular the case when Raney nickel is used under a hydrogen atmosphere of 1 to 20 bar.

The compounds of formulae (II) and (IV) are novel and form part of the invention.

The compound of formula (VII) according to the invention in which $R_2$ represents a protective group, such as an acetyl, benzyl, tert-butoxycarbonyl, benzyloxycarbonyl, trifluoroacetyl, benzoyl, dinitrobenzoyl, neohexanoyl or phthaloyl group, can be prepared from (L)-tyrosine according to the following scheme 4, which reproduces a procedure known in the literature.

Scheme 4

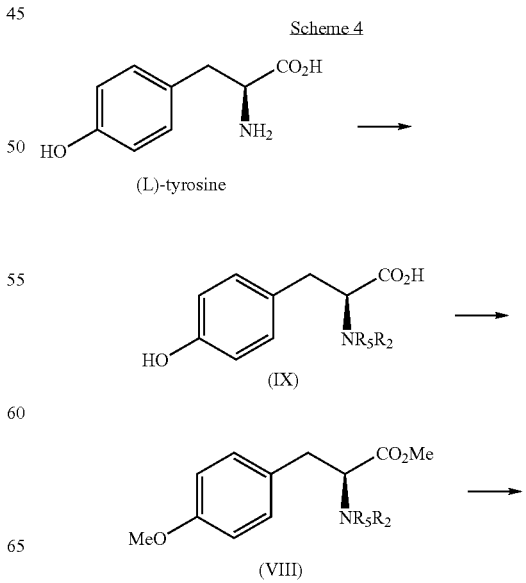

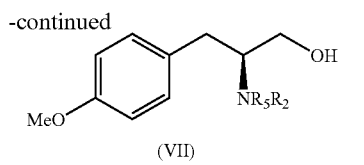

(VII)

According to this scheme 4, (L)-tyrosine can be reacted with acetic anhydride, benzylic anhydride, phthalic anhydride, di(tert-butyl) dicarbonate, benzyl chloroformate, benzyl chloride, neohexanoyl chloride, 3,5-dinitrobenzoyl chloride or methyl trifluoroacetate in a solvent, such as water, at a temperature which can be between 20° C. and 100° C., to produce a compound of formula (IX) in which $R_2$ is as described above. This compound of formula (IX) can subsequently be reacted with a mixture of methyl iodide or of dimethyl sulfate and of potassium carbonate in a solvent, such as acetone, toluene, dimethyl sulfoxide, N,N-dimethyl-acetamide or N,N-dimethylformamide, at a temperature which can be between 20° C. and 100° C., to produce a compound of formula (VIII). During a final stage which makes it possible to produce the compound of formula (VII), use may be made of lithium borohydride or the combinations of sodium borohydride or potassium borohydride with lithium halides (chloride, bromide or iodide).

It is thus clearly apparent that the fact of being able to use (L)-tyrosine, an abundant natural amino acid available in large amounts, as starting material is particularly advantageous. Thus, according to the process of the present invention, the products can be involved in the successive synthetic stages starting from the stage involving (L)-tyrosine until (R)-tamsulosin or one of its pharmaceutically acceptable salts is obtained.

Examples of compounds of formula (IV) of use as intermediates for the synthesis of (R)-tamsulosin and of its pharmaceutically acceptable salts can take in particular the following forms:

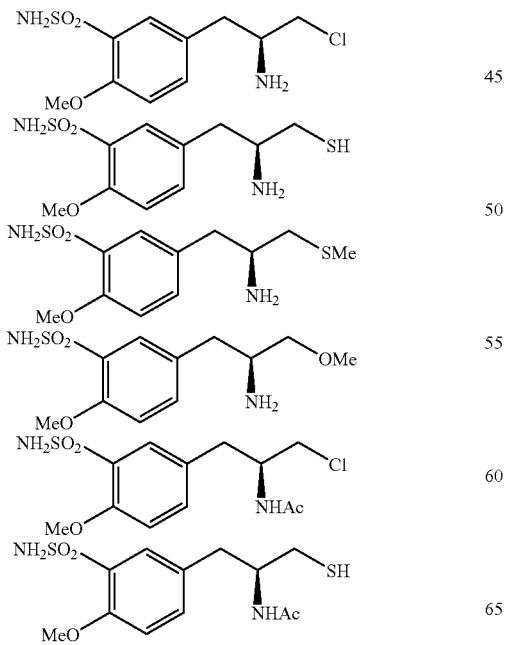

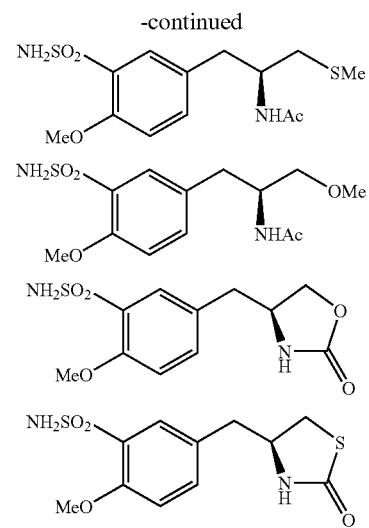

Examples of intermediate compounds of formula (II) of use as intermediates for the synthesis of (R)-tamsulosin and of its pharmaceutically acceptable salts can take in particular the following forms:

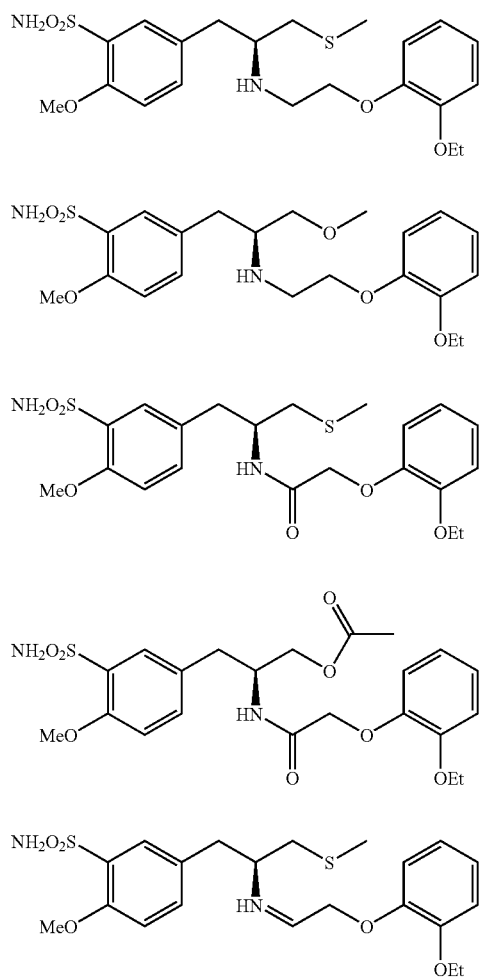

-continued

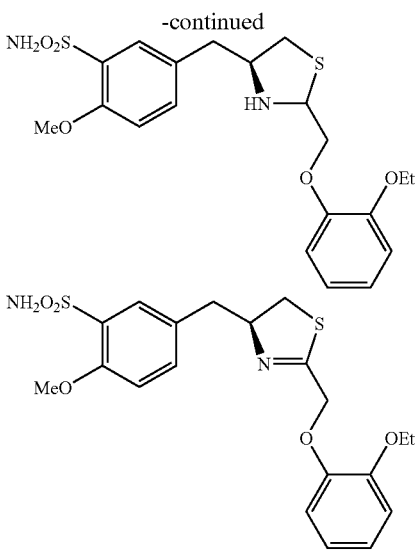

The following examples illustrate the present invention.

EXAMPLE 1

1. (2S)-2-(Acetylamino)-3-(4-hydroxyphenyl)propanoic acid (compound of formula (IX) where $R_2$=acetyl group and $R_5$=hydrogen)

376 ml of acetic anhydride are slowly added to 90.5 g of (L)-tyrosine heated to 90-100° C. in 500 ml of water. After reacting for 2 hours, the medium is cooled to ambient temperature and then concentrated under vacuum. The residue is taken up in 400 ml of acetone, stirred at ambient temperature for 18 hours and then filtered. The filtrate is concentrated under vacuum at 50° C., resulting in (2S)-2-(acetylamino)-3-(4-hydroxyphenyl)-propanoic acid, which is used as is in the following stage.

$^1$H NMR ($d_6$-DMSO): 1.80 (3H, s, COCH$_3$), 2.60-2.90 (2H, AB system, Ar—CH$_2$), 4.30 (1H, m, ArCH$_2$—CH—), 6.65 (2H, d, J=8.4 Hz, Ar—H), 7.01 (2H, d, J=8.4 Hz, Ar—H), 8.13 (1H, d, J=8.0 Hz, NHAc). $[\alpha]_D^{20}$=+33.3 (c=1, MeOH).

2. Methyl (2S)-2-(acetylamino)-3-(4-methoxyphenyl)propanoate (compound of formula (VIII) where $R_2$=acetyl group and $R_5$=hydrogen)

135 g of (2S)-2-(acetylamino)-3-(4-hydroxyphenyl)propanoic acid are dissolved in 270 ml of dimethylformamide. 208.5 g of potassium carbonate and 188 ml of methyl iodide are added to the medium, which is then brought to 50° C. for 18 hours and subsequently cooled to ambient temperature before being filtered. The filtrate is concentrated under vacuum at 50° C., then cooled to ambient temperature and poured onto 810 ml of water. The suspension obtained is cooled in an ice bath and the precipitate is filtered off and then dried under vacuum to result in 83 g of methyl (2S)-2-(acetylamino)-3-(4-methoxyphenyl)propanoate.

$^1$H NMR (CDCl$_3$): 1.90 (3H, s, COCH$_3$), 3.04-3.08 (2H, AB system, Ar—CH$_2$), 3.70 (3H, s, CO$_2$CH$_3$), 3.80 (3H, s, ArOCH$_3$), 4.80 (1H, m, ArCH$_2$—CH—), 5.90 (1H, d, J=8.0 Hz, NHAc), 6.80 (2H, d, J=8.6 Hz, Ar—H), 7.0 (2H, d, J=8.6 Hz, Ar—H). $[\alpha]_D^{20}$=+26.3 (c=1, MeOH).

3. N-[(1S)-2-Hydroxy-1-(4-methoxybenzyl)ethyl]acetamide (compound of formula (VII) where $R_2$=acetyl group and $R_5$=hydrogen)

17.4 g of lithium borohydride and then 50 ml of methanol are slowly added at ambient temperature to a solution of 50 g of methyl (2S)-2-(acetylamino)-3-(4-methoxyphenyl)propanoate in 500 ml of tetrahydrofuran under an inert atmosphere. The reaction medium is stirred at ambient temperature for 18 hours and is then hydrolyzed with an aqueous ammonium chloride solution. The precipitate is filtered off and the filtrate is concentrated under vacuum at 50° C. The residue is taken up in 200 ml of ethyl acetate and washed with 50 ml of water, and the organic phase is concentrated under vacuum, resulting in 35.5 g of N-[(1S)-2-hydroxy-1-(4-methoxybenzyl)ethyl]acetamide.

$^1$H NMR ($d_6$-DMSO): 1.74 (3H, s, COCH$_3$), 2.40-2.80 (2H, AB system, Ar—CH$_2$), 3.20-3.40 (2H, m, CH$_2$OH), 3.70 (3H, s, ArOCH$_3$), 3.80 (1H, m, ArCH$_2$—CH—), 6.80 (2H, d, J=8.6 Hz, Ar—H), 7.1 (2H, d, J=8.6 Hz, Ar—H), 7.89 (1H, d, J=8.2 Hz, NHAc). $[\alpha]_D^{20}$=−28.8 (c=1, MeOH).

3.1. (2S)-2-N-tert-Butoxycarbonylamino-3-(4-methoxyphenyl)propan-1-ol (compound of formula (VII) where $R_2$=tert-butoxycarbonyl and $R_5$=hydrogen)

This derivative is obtained in the same way as the compound mentioned above in 3. from (L)-tyrosine by a procedure alike in all respects, with the exception of the use of di(tert-butyl)dicarbonate instead of acetic anhydride.

$^1$H NMR (CDCl$_3$): 1.43 (9H, s, C(CH$_3$)$_3$), 3.04-3.08 (2H, d, J=7.0 Hz, Ar—CH$_2$), 3.50-3.70 (2H, m, CH$_2$OH), 3.80 (3H, s, ArOCH$_3$), 3.90 (1H, m, ArCH$_2$—CH—), 4.81 (1H, d, J=8.0 Hz, NHAc), 6.85 (2H, d, J=8.6 Hz, Ar—H), 7.1 (2H, d, J=8.6 Hz, Ar—H).

3.2. (2S)-2-N-Phthalimido-3-(4-methoxyphenyl)propan-1-ol (compound of formula (VII) where $R_2$ and $R_5$=phthalimido)

This derivative is obtained in the same way as the compound mentioned above in 3. from (L)-tyrosine by a procedure alike in all respects, with the exception of the use of phthalic anhydride instead of acetic anhydride.

$^1$H NMR ($d_6$-DMSO): 2.98-3.07 (2H, AB system, Ar—CH$_2$), 3.63 (3H, s, ArOCH$_3$), 3.70 (1H, m, ArCH$_2$—CH—), 3.91-4.40 (2H, m, CH$_2$OH), 6.74 (2H, d, J=8.6 Hz, Ar—H), 7.03 (2H, d, J=8.6 Hz, Ar—H), 7.79 (4H, s, Ar—H).

3.3. (2S)-2-Amino-3-(4-methoxyphenyl)propan-1-ol (compound of formula (VII) where $R_2$ and $R_5$=hydrogen)

This derivative was obtained from (L)-O-methyltyrosine in accordance with the procedure described in Organic Syntheses, vol. 68, pp. 77-82 (1990), by reduction with the borane-dimethyl sulfide complex.

$^1$H NMR (D$_2$O): 2.60-2.90 (2H, AB system, Ar—CH$_2$), 3.30-3.50 (2H, m, CH$_2$OH), 3.60 (1H, m, ArCH$_2$—CH—), 3.61 (3H, s, ArOCH$_3$), 6.85 (2H, d, J=8.6 Hz, Ar—H), 7.15 (2H, d, J=8.6 Hz, Ar—H).

3.4. (4S)-4-(4-Methoxybenzyl)-2-oxazolidinone (compound of formula (Vb) where Q and W=oxygen)

This derivative was obtained from the preceding compound in the presence of diethyl carbonate in accordance with the procedure described in Organic Syntheses, vol. 68, pp. 77-82 (1990).

$^1$H NMR (CDCl$_3$): 2.77-2.85 (2H, AB system, Ar—CH$_2$), 3.77 (3H, s, ArOCH$_3$), 4.01-4.16 (2H, m, CH$_2$OH), 4.37 (1H, pseudo t, ArCH$_2$—CH—), 6.55 (1H, s, NHAc), 6.85 (2H, d, J=8.5 Hz, Ar—H), 7.09 (2H, d, J=8.5 Hz, Ar—H).

3.5. 2-((2S)-2-N-Acetyl-(4-methoxyphenyl)propyl)-1-cyclohexyl-3-isoureido-cyclohexyl (compound of formula (VIb) where $R_2$=acetyl group, —$OR_4$=dicyclohexylisourea and $R_5$=hydrogen)

10 g of (2S)-2-N-acetyl-amino-3-(4-methoxyphenyl)propan-1-ol are heated at 80° C. for 6 h in 25 ml of N,N-dimethylformamide in the presence of 9.25 g of dicyclohexylcarbodiimide and 44 mg of cuprous chloride. After returning to ambient temperature, 70 ml of water are added and extraction is carried out with ethyl acetate. The organic phase is washed with an aqueous ammonia solution and then with water, dried over magnesium sulfate and concentrated under vacuum. 12.62 g of the dicyclohexylisourea are collected.

$^1$H NMR (CDCl$_3$): 1.22-2.04 (22H, m, c-Hex), 2.06 (3H, s, COCH$_3$), 2.53-3.09 (2H, AB system, OCH$_2$C(N)NH), 3.48-3.62 (2H, m, Ar—CH$_2$), 3.79 (3H, s, ArOCH$_3$), 4.01 (1H, m, ArCH$_2$—CH—), 6.83 (2H, d, J=8.5 Hz, Ar—H), 7.20 (2H, d, J=8.5 Hz, Ar—H), 8.58 (1H, d, J=8.2 Hz, NHAc).

3.6. Acetate of (2S)-2-N-tert-butoxycarbonylamino-3-(4-methoxyphenyl)propan-1-yle (compound of formula (VIb) where $R_2$=tert-butoxycarbonyl, $R_4$=acetyl group and $R_5$=hydrogen)

This derivative is obtained by reacting 10 g of (2S)-2-N-tert-butoxycarbonylamino-3-(4-methoxyphenyl)propan-1-ol in 100 ml of dichloromethane with 3.07 g of acetyl chloride and 7.2 g of triethylamine at 20° C. in the presence of a catalytic amount of 4-dimethylaminopyridine. After reacting for 18 hours, 50 ml of water are added to the medium and the organic phase is washed with a dilute copper sulfate solution, then dried over magnesium sulfate and concentrated under vacuum. 9.77 g of the acetate are finally collected.

$^1$H NMR (CDCl$_3$): 1.42 (9H, s, C(CH$_3$)$_3$), 2.09 (3H, s, COCH$_3$), 2.67-2.88 (2H, AB system, Ar—CH$_2$), 3.78 (3H, s, ArOCH$_3$), 4.02-4.11 (2H, AB system, CH$_2$OAc), 4.37 (1H, m, ArCH$_2$—CH—), 5.61 (1H, d, J=8.0 Hz, NHBOc), 6.83 (2H, d, J=8.6 Hz, Ar—H), 7.09 (2H, d, J=8.6 Hz, Ar—H).

3.7. para-Toluenesulfonate of (2S)-2-N-tert-butoxy-carbonylamino-3-(4-methoxyphenyl)propan-1-yle (compound of formula (VIb) where $R_2$=tert-butoxycarbonylamino, $R_4$=para-toluenesulfonyl and $R_5$=hydrogen)

This derivative is obtained in the same way as the abovementioned compound from (2S)-2-N-tert-butoxy-carbonyl-3-(4-methoxyphenyl)propan-1-ol by a procedure alike in all respects, with the exception of the use of para-toluenesulfonyl chloride instead of acetyl chloride.

$^1$H NMR (CDCl$_3$): 1.41 (9H, s, C(CH$_3$)$_3$), 2.39 (3H, s, ArCH$_3$), 2.68-2.72 (2H, AB system, Ar—CH$_2$), 3.60 (1H, m, ArCH$_2$—CH—), 3.75 (3H, s, ArOCH$_3$), 3.95 (2H, d, J=4.9 Hz, CH$_2$OTos), 5.39 (1H, d, J=8.0 Hz, NHAc), 6.70 (2H, d, J=8.6 Hz, Ar—H), 6.92 (2H, d, J=8.6 Hz, Ar—H), 7.19 (2H, d, J=8.2 Hz, Ar—H), 7.62 (2H, d, J=8.2 Hz, Ar—H).

3.8. (S)-2-Acetylamino-3-(4-methoxyphenyl)propyl trifluoroacetate (compound of formula (VIb) where $R_4$=trifluoroacetyl and $R_2$=acetyl)

7.1 g of trifluoroacetic anhydride are added to a suspension of 6.9 g of N-[(1S)-2-hydroxy-1-(4-methoxybenzyl)ethyl]-acetamide in 14 ml of methyl tert-butyl ether under an inert atmosphere. The medium is brought to 40° C. for 1 hour. 21 ml of heptane are added to the reaction medium. The product is filtered off after having cooled the suspension to –10° C. After drying, 8.2 g of (S)-2-acetylamino-3-(4-methoxy-phenyl)propyl trifluoroacetate are obtained.

$^1$H NMR (CDCl$_3$): 1.97 (3H, s, COCH$_3$), 1.79-2.86 (2H, AB system, Ar—CH$_2$), 3.79 (3H, s, ArOCH$_3$), 4.27-4.34 (2H, AB system, CH$_2$OCOCF$_3$), 4.50 (1H, m, ArCH$_2$—CH—), 5.75 (1H, d, J=8.5 Hz, NHAc), 6.85 (2H, d, J=8.6 Hz, ArH), 7.09 (2H, d, J=8.6 Hz, ArH)

3.9. N-[(1S)-2-Chloro-1-(4-methoxybenzyl)ethyl]acetamide (compound of formula (VIa) where $R_2$=acetyl group, X=chlorine and $R_5$=hydrogen)

A suspension composed of 7.6 g of (S)-2-acetylamino-3-(4-methoxyphenyl)propyl trifluoroacetate and of 1.1 g of lithium chloride in 7.6 ml of N-methylpyrrolidone is brought to 80° C. for 2 hours. The solution obtained is generally used directly in carrying out the following stage.

$^1$H NMR (CDCl$_3$): 1.95 (3H, s, COCH$_3$), 2.80 (2H, broad s, Ar—CH$_2$), 3.40-3.60 (2H, AB system, CH$_2$Cl), 3.80 (3H, s, ArOCH$_3$), 4.40 (1H, m, ArCH$_2$—CH—), 5.70 (1H, d, J=8.2 Hz, NHAc), 6.80 (1H, d, J=8.5 Hz, Ar—H), 7.16 (2H, d, J=8.5 Hz, Ar—H). $[\alpha]_D^{20}$=–46.6 (c=1, CHCl$_3$)

3.10. N-[(1S)-1-(4-Methoxybenzyl)-2-(methylthio)ethyl]-acetamide (compound of formula (V) where $R_2$=acetyl group and $R_5$=hydrogen)

The N-[(1S)-2-chloro-1-(4-methoxybenzyl)ethyl]acetamide in solution in N-methylpyrrolidone prepared in the preceding stage is added to a suspension of sodium thiomethoxide (1.8 g) in 3.8 ml of N-methylpyrrolidone at 20° C. The reaction medium is brought to 40° C. for 2 hours. The product formed is precipitated by addition of 5.7 ml of water. After filtration and drying, 3.7 g of N-[(1S)-1-(4-methoxybenzyl)-2-(methylthio)ethyl]acetamide are isolated.

$^1$H NMR (CDCl$_3$): 1.94 (3H, s, COCH$_3$), 2.10 (3H, s, SCH$_3$), 2.58 (2H, d, J=5.6 Hz, Ar—CH$_2$), 2.83 (2H, d, J=6.6 Hz, CH$_2$SMe), 3.77 (3H, s, ArOCH$_3$), 4.27 (1H, m, ArCH$_2$—CH—), 6.0 (1H, d, J=8.2 Hz, NHAc), 6.82 (1H, d, J=8.5 Hz, Ar—H), 7.11 (1H, d, J=8.5 Hz, Ar—H). $[\alpha]_D^{20}$=+11.8 (c=0.5, CHCl$_3$).

4. N-[(1S)-2-Chloro-1-(4-methoxybenzyl)ethyl]acetamide (Compound of Formula (VIa) Where $R_2$=acetyl Group, X=chlorine and $R_5$=hydrogen)

72 ml of thionyl chloride are slowly added at ambient temperature to a suspension of 200 g of N-[(1S)-2-hydroxy-1-(4-methoxybenzyl)ethyl]acetamide in 1 liter of toluene. The medium is subsequently heated at reflux for 2 hours and is then cooled to ambient temperature, and the solvent is evaporated under vacuum. The residue is subsequently taken up in 800 ml of water and cooled to ambient temperature. The resulting suspension is filtered and the solid is washed with water and then dried at 40° C. under vacuum. 119.1 g of N-[(1S)-2-chloro-1-(4-methoxybenzyl)ethyl]acetamide are thus collected.

$^1$H NMR (CDCl$_3$): 1.95 (3H, s, COCH$_3$), 2.80 (2H, broad s, Ar—CH$_2$), 3.40-3.60 (2H, AB system, CH$_2$Cl), 3.80 (3H, s, ArOCH$_3$), 4.40 (1H, m, ArCH$_2$—CH—), 5.70 (1H, d, J=8.2 Hz, NHAc), 6.80 (1H, d, J=8.5 Hz, Ar—H), 7.16 (2H, d, J=8.5 Hz, Ar—H). $[\alpha]_D^{20}$=–46.6 (c=1, CHCl$_3$).

5. N-[(1S)-1-(4-Methoxybenzyl)-2-(methylthio)ethyl]-acetamide (compound of formula (V) where $R_2$=acetyl group and $R_5$=hydrogen)

4 g of sodium thiomethoxide are added at 0-5° C. to a solution of 13.8 g of N-[(1S)-2-chloro-1-(4-methoxybenzyl)ethyl]acetamide in 60 ml of tetra-hydrofuran. After returning to ambient temperature, the suspension is filtered and the solid is washed with 2×10 ml of tetrahydrofuran. The filtrate is concentrated to dryness, providing 14 g of N-[(1S)-1-(4-methoxybenzyl)-2-(methylthio)ethyl]acetamide.

$^1$H NMR (CDCl$_3$): 1.94 (3H, s, COCH$_3$), 2.10 (3H, s, SCH$_3$), 2.58 (2H, d, J=5.6 Hz, Ar—CH$_2$), 2.83 (2H, d, J=6.6 Hz, CH$_2$SMe), 3.77 (3H, s, ArOCH$_3$), 4.27 (1H, m, ArCH$_2$—CH—), 6.0 (1H, d, J=8.2 Hz, NHAc), 6.82 (1H, d, J=8.5 Hz, Ar—H), 7.11 (1H, d, J=8.5 Hz, Ar—H). $[\alpha]_D^{20}$=+11.8 (c=0.5, CHCl$_3$).

6. 2-(2S)-N-Acetyl-3-(4-methoxyphenyl)propane-1-isothiourea (compound of formula (Va) where $R_2$=acetyl group, —$SR_4$=isothiourea and $R_5$=hydrogen)

A solution of 5 g of N-[(1S)-2-chloro-1-(4-methoxy-benzyl)ethyl]acetamide in 10 ml of ethanol comprising 0.63 ml of water is heated at reflux for 1 hour in the presence of 1.59 g of thiourea. The solvents are subsequently concentrated under vacuum, the residue is taken up in 100 ml of water and the pH is adjusted to 8 with an aqueous sodium hydrogencarbonate solution. Extraction is carried out with ethyl acetate and the organic phase is concentrated to dryness to collect 4.6 g of the isothiourea.

$^1$H NMR (d$_6$-DMSO): 2.32 (3H, s, COCH$_3$), 3.10-3.40 (2H, m, CH$_2$S—), 3.90 (1H, m, ArCH$_2$—CH—), 4.30-4.70 (2H, m, Ar—CH$_2$), 4.22 (3H, s, ArOCH$_3$), 7.35 (2H, d, J=8.6 Hz, Ar—H), 7.66 (2H, d, J=8.6 Hz, Ar—H), 8.3 (1H, d, J=8.2 Hz, NHAc)

7. 5-[(2S)-2-(Acetylamino)-3-(methylthio)propyl]-2-methoxybenzenesulfonyl chloride (compound of formula (IVa) where $R_2$=acetyl group, $R_3$=chlorine and $R_5$=hydrogen)

A solution of 38 g of N-[(1S)-1-(4-methoxybenzyl)-2-(methylthio)ethyl]acetamide in 40 ml of thionyl chloride is slowly run onto 40 ml of chlorosulfonic acid at 0° C. The medium is allowed to return to ambient temperature and is then hydrolyzed with 120 g of ice. The resulting aqueous phase is extracted with 2×100 ml of dichloromethane and the latter is washed with 2×100 ml of water, dried over magnesium sulfate, filtered and concentrated under vacuum. 42.6 g of 5-[(2S)-2-(acetylamino)-3-(methylthio)propyl]-2-methoxybenzenesulfonyl chloride are collected.

$^1$H NMR (CDCl$_3$): 1.95 (3H, s, COCH$_3$), 2.13 (3H, s, SCH$_3$) 2.62 (2H, d, J=5.9 Hz, Ar—CH$_2$), 2.79-3.03 (2H, AB system, CH$_2$SMe), 4.04 (3H, s, ArOCH$_3$), 4.31 (1H, m, ArCH$_2$—CH—), 6.0 (1H, d, J=8.4 Hz, NHAc), 7.08 (1H, d, J=8.6 Hz, Ar—H), 7.58 (1H, dd, J=8.6 and 2.2 Hz, Ar—H), 7.77 (1H, d, J=2.2 Hz, Ar—H). $[\alpha]_D^{20}$=+5.8 (c=0.4, CHCl$_3$).

8. N-[(1S)-1-[3-(Aminosulfonyl)-4-methoxybenzyl]-2-(methylthio)ethyl]acetamide (compound of formula (IVa') where $R_2$=acetyl group, $R_3$=amino group and $R_5$=hydrogen)

37 ml of 27% aqueous ammonia are added to a solution of 45 g of 5-[(2S)-2-(acetylamino)-3-(methylthio)propyl]-2-methoxybenze-nesulfonyl chloride in 200 ml of tetrahydrofuran at 0-5° C. The temperature is allowed to gradually return to ambient temperature and then medium is then concentrated to dryness. The residue is taken up in 400 ml of dichloromethane at reflux and is then cooled to 0° C. After filtration and drying, 40 g of N-[(1S)-1-[3-(aminosulfonyl)-4-methoxybenzyl]-2-(methylthio)ethyl]acetamide are collected.

$^1$H NMR (d$_6$-DMSO): 1.75 (3H, s, COCH$_3$), 2.05 (3H, s, SCH$_3$), 2.47-2.56 (2H, AB system, Ar—CH$_2$), 2.53-2.83 (2H, AB system, CH$_2$SMe), 3.87 (3H, s, ArOCH$_3$), 3.96 (1H, m, ArCH$_2$—CH—), 7.02 (2H, broad s, SO$_2$NH$_2$), 7.11 (1H, d, J=8.5 Hz, Ar—H), 7.39 (1H, dd, J=8.5 and 2.1 Hz, Ar—H), 7.57 (1H, d, J=2.1 Hz, Ar—H), 7.89 (1H, d, J=8.5 Hz, NHAc). $[\alpha]_D^{20}$=+24.7 (c=0.4, MeOH).

9. 5-[(2S)-2-Amino-3-(methylthio)propyl]-2-methoxybenzenesulfonamide hydrochloride (compound of formula (IVa") where $R_3$=amino group and $R_2$ and $R_5$=hydrogen)

17.4 g of N-[(1S)-1-[3-(aminosulfonyl)-4-methoxy-benzyl]-2-(methylthio)ethyl]acetamide are heated at reflux for 18 hours in 85 ml of 5N HCl. After cooling to 0-5° C., the suspension is filtered off and the precipitate is washed with water and then taken up in 30 ml of acetone. After stirring at ambient temperature for one hour, the precipitate is again filtered off and dried under vacuum at 70° C. 11 g of 5-[(2S)-2-amino-3-(methylthio)propyl]-2-methoxybenzenesulfonamide hydrochloride are collected.

$^1$H NMR (d$_6$-DMSO): 2.06 (3H, s, SCH$_3$), 2.60-2.80 (2H, AB system, Ar—CH$_2$), 2.85-3.15 (2H, AB system, CH$_2$SMe), 3.46 (1H, m, ArCH$_2$—CH—), 3.87 (3H, s, ArOCH$_3$), 7.08 (2H, broad s, SO$_2$NH$_2$), 7.17 (1H, d, J=8.5 Hz, Ar—H), 7.49 (1H, dd, J=8.5 and 2.1 Hz, Ar—H), 7.61 (1H, d, J=2.1 Hz, Ar—H), 8.38 (3H, broad s, NH$_3^+$). $[\alpha]_D^{20}$=+22.2 (c=0.1, H$_2$O).

10.1. 2-Methoxy-5-{(2S)-2-[2-(2-ethoxyphenoxy)ethylamino]-3-(methylthio)propyl}benzenesulfonamide (compound of formula (II) where Q=sulfur, $R_3$=—NH$_2$ and $R_4$=methyl)

A solution of 5.51 g of o-ethoxyphenoxyacetaldehyde ethyl acetal in 20 ml of THF is heated at reflux for 6 hours in the presence of 3 ml of water and of 3 ml of concentrated hydrochloric acid. After cooling to ambient temperature, the medium is dried over MgSO$_4$ and filtered. The filtrate obtained is subsequently run slowly onto a solution of 5.25 g of 5-[(2S)-2-amino-3-(methylthio)propyl]-2-methoxybenzenesulfonamide hydrochloride and of 3 g of sodium cyanoborohydride in 70 ml of methanol. The reaction is continued for 24-48 hours, then 5 ml of 2N HCl are added to the medium and the medium is concentrated to dryness. The residue is taken up in the minimum amount of water and the pH is adjusted to 7 with NaHCO$_3$. This aqueous phase is extracted with ethyl acetate and then the organic phases are dried over MgSO$_4$, filtered and concentrated under vacuum. The crude oil obtained is chromatographed on silica gel, elution being carried out with a heptane/ethyl acetate gradient. 4 g of 2-methoxy-5-{(2S)-2-[2-(2-ethoxyphenoxy)ethylamino]-3-(methylthio)-propyl}benzenesulfonamide are obtained.

$^1$H NMR (d$_6$-DMSO): 1.30 (3H, t, J=6.9 Hz, ArOCH$_2$CH$_3$), 2.06 (3H, s, SCH$_3$), 2.65 (2H, m, Ar—CH$_2$), 2.75-3.0 (2H, AB system, CH$_2$SMe), 3.15-3.40 (4H, m, N—CH$_2$CH$_2$—O), 3.85 (3H, s, ArOCH$_3$), 4.05 (2H, q, J=6.9 Hz, ArOCH$_2$CH$_3$), 4.10 (1H, m, ArCH$_2$—CH—), 6.80-6.95 (4H, m, Ar—H), 7.05 (2H, broad s, SO$_2$NH$_2$), 7.15 (1H, d, J=8.5 Hz, Ar—H), 7.49 (1H, dd, J=8.5 and 2.1 Hz, Ar—H), 7.65 (1H, d, J=2.1 Hz, Ar—H). $[\alpha]_D^{20}$=−25.4 (c=1.0, EtOH).

10.2. 2-Methoxy-5-{(2S)-2-[2-(2-ethoxyphenoxy)acetamido]-3-acetoxypropyl}benzenesulfonamide (noncyclic compound of formula (II) where Q=O, $R_4$=acetyl and Y=C=O)

3.35 g of triethylamine are added to 5 g of 5-[(S)-2-amino-3-acetoxypropyl]-2-methoxybenzenesulfonamide at 0° C. in 25 ml of N,N-dimethylformamide. 3.53 g of 2-ethoxyphenoxyacetyl chloride are subsequently added slowly, the temperature is then allowed to slowly return to ambient temperature, 75 ml of water are added and the aqueous phase is extracted with ethyl acetate. The organic phase is dried over magnesium sulfate and then concentrated to dryness to result in 4.92 g of the amide (II).

$^1$H NMR (CDCl$_3$): 1.31 (3H, t, J=6.9 Hz, O—CH$_2$CH$_3$), 2.1 (3H, s, COCH$_3$), 2.92-3.20 (2H, AB system, Ar—CH$_2$), 3.91 (3H, s, ArOCH$_3$), 4.0 (2H, q, J=6.9 Hz, O—CH$_2$CH$_3$), 4.02-4.11 (2H, AB system, CH$_2$OAc), 4.47 (2H, s, N—C(O)—CH$_2$), 4.84 (1H, m, ArCH$_2$—CH—), 5.50 (2H, broad s, SO$_2$NH$_2$), 6.82-7.02 (4H, m, Ar—H), 7.19 (1H, dd, J=8.6 and 2.2 Hz, Ar—H), 7.51 (1H, d, J=8.6 Hz, Ar—H), 7.62 (1H, d, J=2.2 Hz, Ar—H).

11. (R)-(−)-5-[2-[2-(2-Ethoxyphenoxy)ethylamino]propyl]-2-methoxybenzenesulfonamide hydrochloride ((R)-tamsulosin hydrochloride)

6.8 g of 2-methoxy-5-{(2S)-2-[2-(2-ethoxyphenoxy)ethyl-amino]-3-(methylthio)propyl}benzenesulfonamide in 400 ml of ethanol are heated at 50° C. for 18-24 hours in the presence of 30 g of Raney nickel. After returning to ambient temperature, the catalyst is filtered off, the pH of the filtrate is adjusted to 1-2 with a solution of HCl in isopropanol and then the solvent is evaporated under vacuum. The product obtained is subsequently recrystallized from an isopropanol/water mixture, resulting in 3.2 g of (R)-(−)-5-[2-[2-(2-ethoxyphenoxy)ethylamino]propyl]-2-methoxybenzene-sulfonamide hydrochloride.

$^1$H NMR (d$_6$-DMSO): 1.16 (3H, d, J=6.1 Hz, CH—CH$_3$), 1.21 (3H, t, J=6.9 Hz, ArOCH$_2$CH$_3$), 2.71 (1H, pseudo t, Ar—CH$_2$), 3.30-3.70 (5H, m, N—CH$_2$CH$_2$—O+Ar—CH$_2$), 3.89 (3H, s, ArOCH$_3$), 3.97 (2H, q, J=6.9 Hz, ArOCH$_2$CH$_3$), 4.05 (1H, pseudo t, ArCH$_2$—CH—), 6.80-7.06 (4H, m, Ar—H), 7.11 (2H, broad s, SO$_2$NH$_2$), 7.18 (1H, d, J=8.5 Hz, Ar—H), 7.46 (1H, dd, J=8.5 and 2.1 Hz, Ar—H), 7.63 (1H, d, J=2.1 Hz, Ar—H), 9.58 (2H, broad s, NH$_2{}^+$). $[\alpha]_D{}^{24}$=−4.2 (c=0.37, MeOH).

What is claimed is:

1. A compound of formula (II)

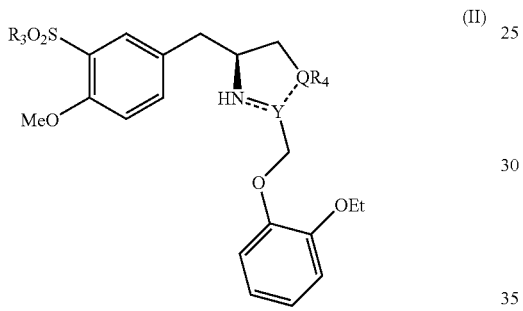

wherein
Q represents an oxygen or sulfur atom,
R$_3$ represents a halogen atom or an —NR$_5$R$_2$ group,
R$_4$ represents a hydrogen atom, a (C$_1$-C$_7$)alkyl, aryl, (C$_1$-C$_7$)acyloyl or aryloyl group, or
QR$_4$ represents an isothiocyanate, or thioamidine group when Q is a sulfur or QR$_4$ represents a (C$_1$-C$_7$)alkylisourea, tri(C$_1$-C$_7$)alkylsilyloxy, tosyloxy, nosyloxy, trifluoroacetyloxy, trifluoromethanesulfonyloxy or mesyloxy group when Q is an oxygen,
R$_5$ and R$_2$ represent, simultaneously or independently of one another, a hydrogen atom or a (C$_1$-C$_7$)alkyl, aryl, (C$_1$-C$_7$)alkylaryl, (C$_1$-C$_7$)acyloyl, aryloyl, (C$_1$—C$_7$) alkyloxycarbonyl or aryloxycarbonyl group,
—NR$_5$R$_2$ can also represent an —NHR$_2$ group where R$_2$ is a protective group,
- - - - - means that there does not exist a bond so as to form a ring,
Y represents

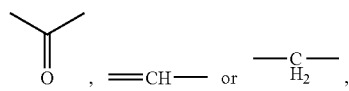

means that there exists a single bond.

2. The compound of formula (II) as claimed in claim 1, corresponding to any one of the following formulae:

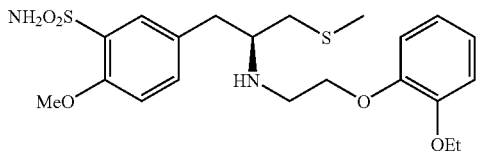

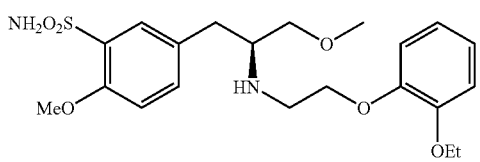

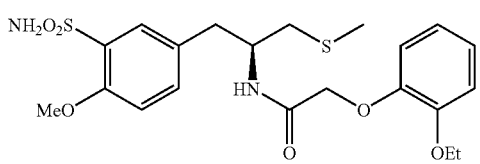

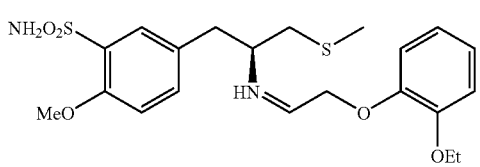

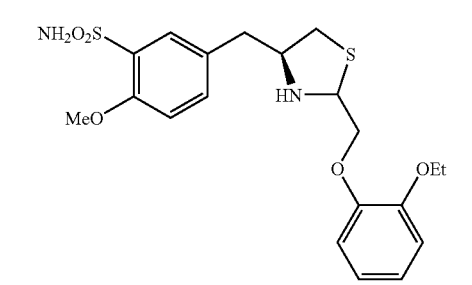

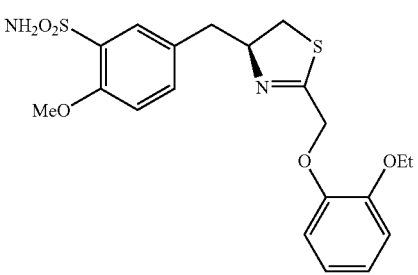

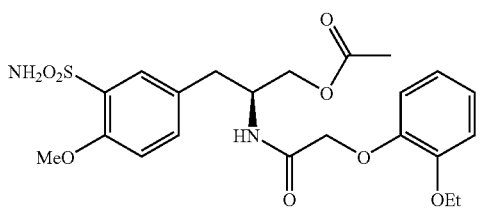

3. A method for the preparation of a compound of claim 1 of formula (II)

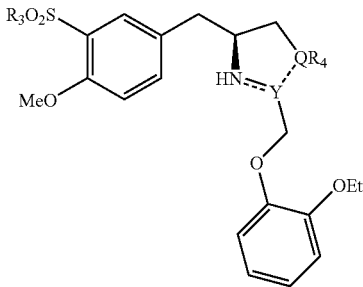

in which
Q represents an oxygen or sulfur atom,
$R_3$ represents a halogen atom or an —$NR_5R_2$ group,
$R_4$ represents a hydrogen atom, a ($C_1$-$C_7$)alkyl, aryl, ($C_1$-$C_7$)acyloyl or aryloyl group, or
$QR_4$ represents an isothiocyanate, or thioamidine group when Q is a sulfur or $QR_4$ represents a ($C_1$-$C_7$)alkylisourea, tri($C_1$-$C_7$)alkylsilyloxy, tosyloxy, mesyloxy, nosyloxy, trifluoromethanesulfonyloxy or trifluoroacetyloxy group when Q is an oxygen,
$R_5$ and $R_2$ represent, simultaneously or independently of one another, a hydrogen atom or a $C_1$-$C_7$)alkyl, aryl, ($C_1$-$C_7$)alkylaryl, $C_1$-$C_7$)acyloyl, aryloyl, ($C_1$-$C_7$)alkyloxycarbonyl or aryloxycarbonyl group,
—$NR_5R_2$ can also represent an —$NHR_2$ group where $R_2$ is a protective group,
- - - - - means that there does not exist a bond so as to form a ring,
Y represents

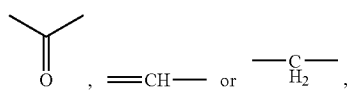

means that there exists a single bond,
wherein a compound of formula (IV)

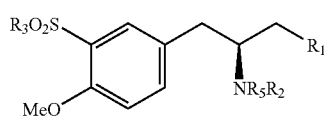

in which
$R_1$ represents a halogen or an —$SR_4$ or —$OR_4$ group,
$R_2$ and $R_5$ are as defined above and
$R_3$ is as defined above,
is reacted by coupling with a compound of formula (III)

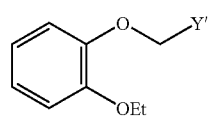

in which
Y' represents a —$CO_2H$, —COCl, —CHO, —$CH_2Cl$, —$CH_2Br$ or —$CH_2I$ group when the coupling takes place with a compound of formula (IV) for which $R_1$ is a —$SR_4$ or —$OR_4$ group,
or Y' represents a —CHO group when the coupling takes place with a compound of formula (IV) for which $R_1$ is a —SH or $SR_4$ group,
or Y' represents a —COCl, —$CH_2Cl$, —$CH_2Br$ or —$CH_2I$ group when the coupling takes place with a compound of formula (IV) for which the $R_1$ and $R_2$ groups together form an oxazolidin-2-one, a thiazolidin-2-one or a thiazolidine-2-thione,
or, finally, Y' represents a —$CS_2Na$ group when the coupling takes place with a compound of formula (IV) for which $R_1$ is a halogen atom or a leaving group.

4. The method as claimed in claim 3, wherein the protective group is chosen from an acetyl, benzyl, tert-butoxycarbonyl, benzyloxycarbonyl, trifluoroacetyl, benzoyl, neohexanoyl, dinitrobenzoyl and phthaloyl group.

5. The method as claimed in claim 3, wherein a compound of formula (IV)

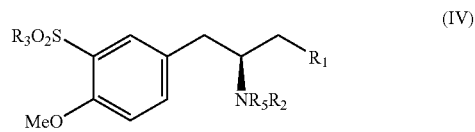

in which
$R_1$ represents an —$SR_4$ or —$OR_4$ group and
$R_2$, $R_3$, $R_4$ and $R_5$ are as defined in claim 3,
is reacted by coupling with a compound of formula (III)

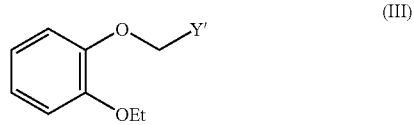

in which
Y' represents a —$CO_2H$, —COCl, —CHO, —$CH_2Cl$, —$CH_2Br$ or —$CH_2I$ group,
in the presence or absence of a coupling agent.

6. The method as claimed in claim 3, wherein a compound of formula (IV)

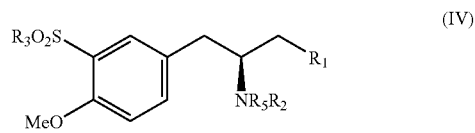

in which
$R_1$ represents an —$SR_4$ or —SH group and
$R_2$, $R_3$ $R_4$ and $R_5$ are as defined in claim 3, is reacted by coupling with a compound of formula (III)

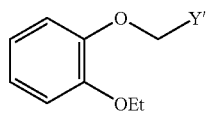
(III)

in which
Y' represents a —CHO group,
in the presence of a reducing agent, or under a hydrogen atmosphere in the presence of a metal catalyst.

7. The method as claimed in claim 3, wherein a compound of formula (IV)

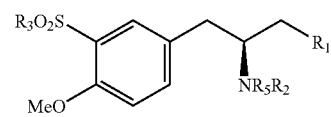
(IV)

in which
$R_1$ represents a halogen atom,
$R_2$, $R_3$ and $R_5$ are as defined in claim 3,
is reacted by coupling with a compound of formula (III)

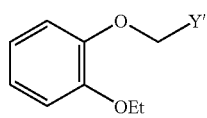
(III)

in which
Y' represents a —$CS_2Na$ group.

8. The method as claimed in claim 3, wherein a compound

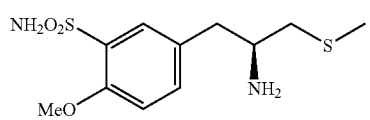

is reacted with a compound of formula

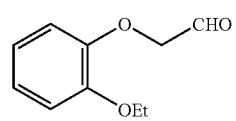

in order to obtain a compound of formula

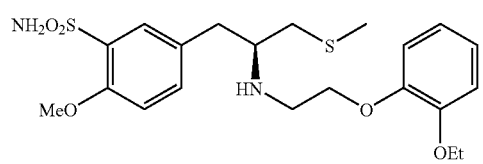

in the presence of a hydride transfer agent, or of a metal catalyst, under a hydrogen atmosphere.

9. A method for the preparation of (R)-tamsulosin or one of its pharmaceutically acceptable salts, wherein (R)-tamsulosin or one of its pharmaceutically acceptable salts is obtained according to the following steps:
reacting by coupling of a compound of formula (IV)

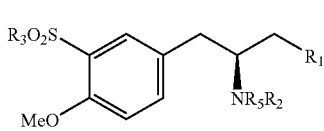
(IV)

in which
$R_1$ represents a halogen or an —$SR_4$ or —$OR_4$ group,
$R_2$ and $R_5$ are as defined
and
$R_3$ is as defined above,
with a compound of formula (III)

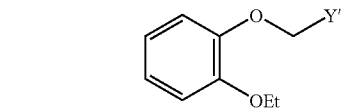
(III)

in which
Y' represents a —$CO_2H$, —COCl, —CHO, —$CH_2Cl$, —$CH_2Br$ or —$CH_2I$ group when the coupling takes place with a compound of formula (IV) for which $R_1$ is a —$SR_4$ or —$OR_4$ group,
or Y' represents a —CHO group when the coupling takes place with a compound of formula (IV) for which $R_1$ is a —SH or —$SR_4$ group,
or Y' represents a —COCl, —$CH_2Cl$, —$CH_2Br$ or —$CH_2I$ group when the coupling takes place with a compound of formula (IV) for which the $R_1$ and $R_2$ groups together form an oxazolidin-2-one, a thiazolidin-2-one or a thiazolidine-2-thione,
or, finally, Y' represents a —$CS_2Na$ group when the coupling takes place with a compound of formula (IV) for which $R_1$ is a halogen atom or a leaving group
to give a compound of claim 1 of formula (II)
desulfurization of the compound of claim 1, when Q is a sulfur atom in the formula (II), or deoxygenation of the compound of claim 1, when Q is an oxygen atom in the formula (II), to obtain (R)-tamsulosin, and
optionally addition of a strong acid to obtain a salt of (R)-tamsulosin.

10. The method as claimed in claim 9, wherein the desulfurization takes place in the presence of Raney nickel/aluminium alloy, of the zinc/nickel chloride alloy or of nickel boride.

11. The method as claimed in claim 3, wherein the coupling takes place with a compound of formula (IV) in which $R_1$ is an —$SR_4$ group as defined in claim 3, wherein it is preceded by a stage in which said compound of formula (IV) is obtained by reaction of a compound of formula (V)

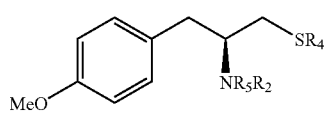
(V)

in which

R$_2$, R$_4$ and R$_5$ are as defined in claim 3, in the presence either of chlorosulfonic acid, on the one hand, or of sulfuric acid or of oleum and then of a chlorinating agent, on the other hand, when R$_3$ of the compound of formula (IV) represents a halogen atom, or after treatment of the latter compound with gaseous ammonia or ammonia in aqueous solution, ammonium carbonate or an organic amine, when R$_3$ of the compound of formula (IV) represents an —NR$_5$R$_2$ group, where R$_5$ and R$_2$ are as defined in claim 3.

12. The method as claimed in claim 3 wherein the compound of formula (IV)

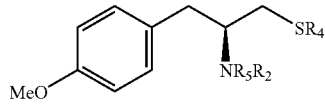
(IV)

is obtained from a compound of formula (V)

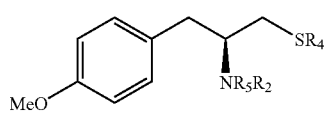
(V)

itself obtained by acylation of a compound of formula (VII)

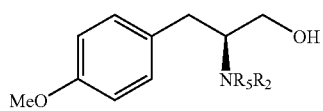
(VII)

resulting in a compound of formula (VIb)

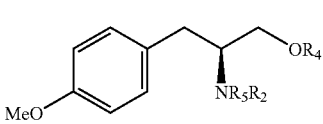
(VIb)

itself subjected to a chlorination reaction, resulting in a compound of formula (VI)

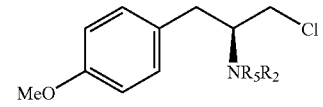
(VI)

itself subjected to a thioalkylation reaction, resulting in said compound of formula (V), the R$_2$, R$_3$, R$_4$ and R$_5$ radicals having the same meanings as those given in claim 3.

* * * * *

UNITED STATES PATENT AND TRADEMARK OFFICE
CERTIFICATE OF CORRECTION

PATENT NO. : 7,619,116 B2  Page 1 of 1
APPLICATION NO. : 10/583472
DATED : November 17, 2009
INVENTOR(S) : Valery Dambrin et al.

It is certified that error appears in the above-identified patent and that said Letters Patent is hereby corrected as shown below:

In the Claims:

At column 22, claim 2, delete the three (3) formulae located between lines numbered 25-55.

At column 22, claim 2, after the first formula, located between lines numbered 5-10, insert -- , --.

At column 22, claim 2, after the second formula, located between lines numbered 10-20, insert -- , --.

At column 22, claim 2, after the third formula, located between lines numbered 20-25, insert -- , or --.

At column 22, claim 2, after the last formula, located between lines numbered 55-65, insert -- . --.

At column 23, claim 3, line numbered 29, change "$C_1$-$C_7$)alkyl" to -- ($C_1$-$C_7$)alkyl --.

At column 23, claim 3, line numbered 30, change "$C_1$-$C_7$)acyloyl" to -- ($C_1$-$C_7$)acyloyl --.

At column 23, claim 3, line numbered 44, change " ___ means that there exists a single bond," to -- ---- means that there exists a single bond, --.

Signed and Sealed this
Twenty-fourth Day of May, 2011

David J. Kappos
*Director of the United States Patent and Trademark Office*